(12) United States Patent
Krishnamoorthy

(10) Patent No.: US 7,378,082 B1
(45) Date of Patent: *May 27, 2008

(54) METHOD FOR TREATING ALLERGIC RHINITIS WITHOUT ADVERSE EFFECTS

(75) Inventor: Ramesh Krishnamoorthy, Cary, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/935,245

(22) Filed: Nov. 5, 2007

(51) Int. Cl.
*A61K 9/12* (2006.01)
*A61K 31/55* (2006.01)

(52) U.S. Cl. .......................... 424/45; 424/43; 424/434; 514/214.02

(58) Field of Classification Search ............ 424/45, 424/43, 434; 514/214.02
See application file for complete search history.

(56) References Cited

U.S. PATENT DOCUMENTS

| | | | |
|---|---|---|---|
| 5,164,194 A * | 11/1992 | Hettche | 424/489 |
| 2002/0037297 A1 | 3/2002 | Crespo et al. | |
| 2003/0050303 A1 | 3/2003 | Trach et al. | |
| 2003/0104017 A1 | 6/2003 | Wada et al. | |
| 2006/0110331 A1 | 5/2006 | Dang et al. | |

FOREIGN PATENT DOCUMENTS

| WO | WO2004/075900 A2 | 9/2004 |
|---|---|---|
| WO | WO 2005/089803 A2 | 9/2005 |
| WO | WO2007/026151 A1 | 3/2007 |

OTHER PUBLICATIONS

"Inspire Announces Positive Results of Phase 2 Trial of Epinastine Nasal Spray for Seasonal Allergic Rhinitis," Press Release, Durham, North Carolina, May 8, 2007.
Office Communication of U.S. Appl. No. 11/770,383, dated Oct. 16, 2007.

* cited by examiner

*Primary Examiner*—Johann Richter
*Assistant Examiner*—Mina Haghighatian
(74) *Attorney, Agent, or Firm*—Howrey LLP; Viola T. Kung

(57) ABSTRACT

The present invention is directed to a method for treating allergic rhinitis without causing an adverse effect of bitter taste. The method comprises administering to a patient an aqueous pharmaceutical formulation comprising 0.1-0.15% (w/v) of epinastine or an acid addition salt thereof, 0.05-0.5% (w/v) of hydroxypropylmethylcellulose to maintain the viscosity between 1.5-10 centipoise, 1-2% (w/v) of propylene glycol, and a buffer to maintain the pH between 5-8, said aqueous epinastine formulation has a tonicity between 200-400 mOsm/kG; the formulation does not contain a sweetening agent. The present invention provides a method for effectively treating allergic rhinitis by delivering a small volume of the epinastine formulation to the nose of a patient using a small volume metered-dose nasal spray pump. The present method does not cause an adverse effect of bitter taste without including sweetening agents in the formulation.

12 Claims, No Drawings

METHOD FOR TREATING ALLERGIC RHINITIS WITHOUT ADVERSE EFFECTS

TECHNICAL FIELD

This invention relates to methods of treating allergic rhinitis by intranasal delivery of a small volume of a viscous epinastine formulation, which does not contain any sweetening agent, whereby the patient perceives a minimal or no bitter taste of epinastine.

BACKGROUND OF THE INVENTION

Epinastine, chemically known as 3-amino-9,13b-dihydro-1H-dibenz-[c,-f]imidazol[1,5-a]azepine, and its acid addition salts are disclosed in German Patent application P 30 08 944.2 which forms the basis for EP 0035749. Methods for the preparation of epinastine are described in EP 0496306 or WO 01/40229. Epinastine is most often used for its antihistaminic effects.

Epinastine hydrochloride (ELASTAT®) has been approved as an eye drop in U.S. for treating allergic conjunctivitis. Epinastine hydrochloride has been approved as an oral tablet in Japan and some South American countries for treating allergic rhinitis. However, especially for children and elderly people, tablets are not always easy to take. It is found that aqueous formulations of epinastine-hydrochloride result in bad taste, reported as bitterness or bitter aftertaste.

The bitter taste of epinastine is strong. Many attempts have been made to reduce the bitter taste of epinastine. Prior art methods all involve using taste masking agents, particularly sweetening agents to mask the bitter taste of epinastine.

US2003/0104017 discloses a pharmaceutical formulation comprising epinastine or an acid addition salt thereof, and at least two kinds of sweeteners or flavoring agents, wherein one of the at least two kinds of sweeteners or flavoring agents masks the quick-acting bitterness of epinastine or its salt and the other one masks the long-acting bitterness of epinastine or its salt.

WO2004/075900 discloses pharmaceutical powder formulation comprising epinastine, sodium lauryl sulfate, sweetening agents and/or flavoring agents.

US2003/0050303 broadly discloses a method for inhibiting the influx of neutrophils and eosinophils into the tissue of the ocular conjunctiva or the nasal mucous membrane in a host, the method comprising topically administering to a host in need of such treatment an aqueous solution comprising epinastine, optionally in the form of its racemate, its enantiomers, or its pharmacologically acceptable acid addition salts thereof, in a concentration of 0.005 to 0.5 mg/ml of solution. The reference did not mention the problem of bitter taste of epinastine nor provided a solution to it.

Azelastine hydrochloride is another antihistamine with an even worse taste (extremely bitter and pungent taste) than epinastine at a much lower concentration. ASTELIN® (0.1% azelastine hydrochloride) nasal spray was approved for treating allergic rhinitis in the United States. When ASTELIN® was administered to subjects at 137 μL per spray, two sprays per nostril, twice daily, 19.7% of subjects reported adverse events of bitter taste (see product package insert of ASTELIN® nasal spray).

US2006/0110331 discloses a method for reducing the bitter taste of azalastine by delivering a composition comprising azelastine, hypromellose as a viscosity modifier and at least one taste-masking agent such as sucralose.

Currently, there is not an effective method for treating allergic rhinitis with an aqueous intranasal spray formulation which does not include a taste masking agent such as a sweetening agent. There is a need for an improved aqueous nasal spray formulation for treating allergic rhinitis; such aqueous nasal spray formulation is not only effective to treat allergic rhinitis but also has an acceptable taste profile following repeated dosing.

SUMMARY OF THE INVENTION

The present invention provides a method for treating allergic rhinitis in a subject without causing an adverse effect of bitter taste. The method comprises the steps of: identifying a subject suffering from allergic rhinitis; administering to the nose of the subject one to two sprays at ≦115 μL per nostril per spray once or twice daily of an aqueous epinastine formulation; wherein said aqueous epinastine formulation comprises (a) 0.1-0.15% (w/v) of epinastine or an acid addition salt thereof, (b) 0.05-0.5% (w/v) of hydroxypropylmethylcellulose to maintain the viscosity between 1.5-10 centipoise, (c) 1-2% (w/v) of propylene glycol, and (d) a buffer to maintain the pH between 5-8, said aqueous epinastine formulation has a tonicity between 200-400 mOsm/kG, said formulation does not contain a sweetening agent; whereby the subject perceives a minimal or no bitter taste of said epinastine and the symptoms of allergic rhinitis are reduced.

DETAILED DESCRIPTION OF THE INVENTION

The inventor has unexpectedly discovered an aqueous epinastine formulation that contains a combination of a particular concentration of each ingredient; the formulation can be delivered topically to the nose of an allergic rhinitis patient to treat the patient effectively while the patient only perceives a minimal or no bitter taste. The aqueous epinastine formulation is viscous and has a viscosity of 1.5-10 centipoises. When intranasally delivered in a small volume of ≦120 μL, preferably ≦115 μL, preferably ≦105 μL, preferably ≦90 μL, more preferably ≦85 μL per nostril per spray, the epinastine formulation of the present invention is effective in treating allergic rhinitis, and does not cause a strong bitter aftertaste, even without including taste-masking agents such as sweeteners or flavoring agents in the formulation. Applicants also unexpectedly discovered that when patients are administered with a small volume of 0.1 to 0.15% w/v of epinastine in combination with other ingredients, patients had better sensory attribute scores when sweetening agents are excluded from the formulation.

Although the nose has a large space relative to the spray volume emitted by a small volume metered-dose nasal spray pump, the inventor has discovered that reducing the nasal spray volume from 137 μL (ASTELIN® nasal spray volume) to ≦115 μL, preferably to ≦85 μL, plays an important role in minimizing the bitter aftertaste of epinastine. The inventor has discovered that delivering a small volume of the viscous epinastine formulation of the present invention reduces the bitter aftertaste significantly without compromising the therapeutic efficacy of epinastine. The viscous epinastine formulation is delivered to the nose of a patient using a metered-dose nasal spray pump. The viscous epinastine formulation has minimal post-nasal drip and does not cause an unacceptable quick-acting bitterness or a long-acting bitterness after dosing.

This invention is directed to an aqueous pharmaceutical formulation comprising an antihistamine chemical compound such as epinastine and salts thereof. This invention provides a formulation containing one or more viscosity-enhancing agents that increase the viscosity of the formulation and minimize the bitter taste of epinastine. The formulation does not contain a substantial amount of unacceptable agents for pharmaceutical use, particularly, nasal use. The invention provides a stable aqueous formulation of epinastine; the formulation is suitable for therapeutic uses and remains stable under normal use storage conditions for an extended period of time.

The aqueous pharmaceutical formulations of the present invention exclude the use of inappropriate adjuvants that can cause toxicological outcomes and tissue damage when used in humans or mammals for a long term. The aqueous pharmaceutical formulations of the present invention contain epinastine in solution at sufficient concentrations, and provide an anti-allergic response in mammals. The aqueous pharmaceutical formulations are non-irritating and tolerable to human epithelial cells, and are suitable for multiple instillations.

The present invention is directed to an aqueous pharmaceutical formulation comprising epinastine or a salt thereof, and a viscosity-enhancing agent. Epinastine can be used either as free base or as a pharmaceutically acceptable salt thereof. Preferably, epinastine is used in the form of its acid addition salts such as hydrochloride salt.

"A viscosity-enhancing agent," as used herein, refers to a compound when added to a solution increases the viscosity of the solution. A viscosity-enhancing agent at a suitable concentration can modify or alter the flow properties of the system from a Newtonian fashion (e.g. water) to a pseudo plastic or plastic flow. An increased viscosity alters the residence time, drainage characteristics, and/or bioavailability of the pharmaceutical formulation. A viscosity-enhancing agent typically increases the viscosity of the pharmaceutical formulation 1.5-10 fold (e.g. 1.5-10 centipoises) with respect to water (approximately 1 centipoise).

The viscosity-enhancing agent used in the formulation provides an enhanced viscosity of the formulation without causing precipitation of the active ingredient epinastine or other ingredients, or causing an undesirable flocculation of the final preparation. Furthermore, the viscosity-enhancing agent is compatible with other agents in the formulation. The increased viscosity of the formulation provides a sustained action, minimizes post-nasal drip, and reduces the possibility of the formulation to 'drip back' from the nasal cavity to the back of the throat. By minimizing the postnasal drip and therefore minimizing the amount of preparation that is deposited in the back of the throat wherein the bitter taste of epinastine is less perceived by the subject.

A viscosity-enhancing agent useful for the present invention is often a polymer such as hydroxypropylmethylcellulose, methylcellulose, ethylcellulose, hydroxyethylcellulose, hydroxypropylcellulose, polyvinyl alcohol, and polyvivnyl pyrrolidone. A preferred viscosity-enhancing agent is hydroxypropylmethylcellulose. The viscosity-enhancing agent often improves the physical stability of the formulation. The inventor has discovered that not all typical pharmaceutically acceptable viscosity modifiers are suitable for use in this invention because they are physically incompatible with epinastine in solution and result in flocculation and phase separation, and/or they do not function well at pH 4-8. For example, polyvinyl acrylic acid, polystyrene sulfonic acid, sodium carboxymethylcellulose, xanthan gum, microcrystalline cellulose and sodium carboxymethylcellulose are not suitable for this invention.

Typically, the aqueous pharmaceutical formulation of the present invention comprises 0.001-3% (w/v) epinastine or an acid addition salt thereof, 0.001-0.5% (w/v) viscosity-enhancing agent, a buffer to maintain a pH between 4-8, and a tonicity agent to maintain a tonicity between 200-400 mOsm/kG. The viscosity of the formulation is about 1.5-10 centipoises (cps), preferably 1.5-10 cps, more preferably 2-9 cps, and more preferably 2-6 cps.

The concentration of epinastine in the aqueous formulation is in general 0.001-3%, preferably 0.005-1% or 0.005-0.6%, and more preferably 0.05-0.2%, and most preferably 0.1-0.15% (w/v). For example, a preferred concentration of epinastine is about 0.1% or about 0.15%. The inventor has discovered that epinastine at 0.10-0.15% (w/v) concentration, coupled with 0.05-0.5% (w/v) of hydroxypropylmethylcellulose and 1-2% (w/v) of propylene glycol, and without inclusion of any sweetening agents, when administered to a patient in a small volume of <115 µL, is effective in treating allergic rhinitis without causing an adverse effect of bitter taste. When the epinastine concentration is lower than 0.1% (w/v), e.g., 0.05%, the aqueous formulation is not effective in alleviating the symptoms of allergic rhinitis by the present method. When the epinastine concentration is higher than 0.15% (w/v), e.g., 0.2%, excluding sweetening agents does not provide advantages as to taste perception.

As used in this application, "about" refers to ±15% of the value recited.

The concentration of a viscosity-enhancing agent in the aqueous formulation is in general 0.001-0.5%, preferably 0.05-0.5%, and more preferably 0.1-0.3% (w/v).

The pH of the present formulation is 4-8, preferably 5-8, more preferably 6.0-7.5. Buffers suitable to maintain the pH between 4-8 include phosphate, citrate buffer, acetate buffer, maleate buffer, tartarate buffer, or combination thereof. Phosphate buffer or citrate buffer is preferred. For long-term stability, the formulation is preferred to have a pH of 5-8. Buffers suitable to maintain the pH of 5-8 include citrate buffer, phosphate buffer, citrate/phosphate buffer, maleate buffer, tartarate buffer, or combination thereof. A suitable concentration of the buffer is 1-100 mM, preferably 5-50 mM, more preferably 5-25 mM, and most preferably 10-20 mM.

The tonicity agent is present in an amount to achieve a tonicity between 200-400, preferably 220-380, and more preferably 250-340 mOsm/kG. The tonicity agent can be non-ionic or ionic. A non-ionic tonicity agent is preferred because its compatibility with polymeric adjuvant that functions as a viscosity-enhancing agent. Non-ionic tonicity agents include diols, such as glycerol, mannitol, erythritol; and sugars such as sucrose and dextrose. Other non-ionic tonicity agents such as glycerol, polyethylene glycol, propylene glycol, which also function as cosolvents and taste-masking agent, can also be used. The non-ionic tonicity agent is in general in an amount of 1-20%, preferably 1-10%, more preferably 1-5%. Preferred non-ionic agents are mannitol, sucrose, dextrose, propylene glycol, in an amount of 1-5%. For example, propylene glycol at 1-2% or 1-1.8% (w/v) is a preferred non-ionic tonicity agent for the present invention.

The tonicity agent can also be ionic agents such as sodium chloride, potassium chloride, or a balanced salt solution. The ionic tonicity agents are typically present in an amount of 0.5-0.9%, preferably 0.6-0.9%.

The pharmaceutical formulation of the present invention optionally comprises a chelating agent. A chelating agent is a substance which can form several coordinate bonds to a metal ion. Chelating agents offers a wide range of sequestrants to control metal ions in aqueous systems. By forming stable water-soluble complexes with multivalent metal ions, chelating agents prevent undesired interaction by blocking normal reactivity of metal ions. Ethylenediamine tetraacetate (EDTA), diethylenetriaminepentaacetic acid (DTPA), and N,N-bis(carboxymethyl)glycine (NTA) are examples of chelating agents for the present inventions. EDTA (ethylenediamine tetraacetate) is a preferred chelating agent. The chelating agents are typically present in an amount of 0.01-1%, and preferably 0.02-0.5% w/v.

Health regulations in various countries require that multi-dose ophthalmic and nasal preparations include a preservative. The pharmaceutical formulation of the present invention optionally comprises a preservative. Many well known preservatives that have been used in some other nasal and ophthalmic preparations cannot be used in the present invention, since those preservatives are not considered safe for repeatedly ocular use, or they interact with the viscosity-enhancing agent employed herein to form a complex that reduces the bactericidal activity of the preservative. Suitable preservatives for the present invention include benzalkonium chloride, benzyl alcohol, methyl parabens, propyl parabens, and benzethonium chlorides. In one embodiment, benzalkonium chloride is included as a safe preservative; preferably, benzalkonium chloride is used with EDTA. Typically, preservatives are employed at a level of 0.001-1%, preferably, 0.005-0.25%, and most preferably 0.05-0.2% (w/v).

Taste-masking agents are substances that can mask the undesired taste of a drug. Taste-masking agents include sweeting agents, flavoring agents, or other agents that can mask the taste of a formulation. Sweetening agents, which provide a sweet taste, in general are more effective in masking the bitter taste of a drug than other taste masking agents. Sweetening agents include saccharin sodium, erythritol, aspartame, sucrose, glycerin, sorbitol, glycyrrhinic acid, or glycyrrihinate ammonium salts, and sucralose. Another commonly used sweetening agent is SWEETAM™, which contains monoammonium glycyrrihinate salts pre-blended with suitable adjuvants such as sucrose and dextrose.

However, the inventor has discovered that the aqueous epinastine formulation of the present invention does not cause bitter aftertaste even without including a taste-masking agent such as sweeteners or flavoring agents. Unexpectedly, the inventor further discovered that it is advantageous to exclude sweetening agents from the present formulation as patients perceive better taste when administered with the present formulation containing 0.10-0.15% (w/v) epinastine without a sweetening agent than with a similar formulation with an added sweetening agent.

The inventor has discovered that in a clinical study, the scores reported by patients on smell, satisfaction on smell, taste, satisfaction of taste, bitterness, aftertaste, satisfaction on aftertaste, dryness of nose, and dryness of throat, had a numerical trend that epinastine-unmasked (without a sweetening agent) had better sensory attribute ratings than epinastine-masked (with a sweetening agent). Furthermore, the average score and the individual score of satisfaction on smell of epinastine-unmasked was statistically significantly higher ($p<0.05$) than that of epinastine-masked at 5 minute post dose when the epinastine formulation of the present invention was administered at a target volume of approximately 70 µL. This is unexpected as a person skilled in the art would expect that using a sweetening agent would improve the after taste perceived by patients.

In addition to the clinical advantages, there are other advantages when excluding a sweetening agent in the formulation. One may encounter fewer problems with regulatory approval processes with one less unnecessary ingredient. The raw material cost and the manufacturing cost are also reduced without a sweetening agent.

The viscosity-enhancing agent, the tonicity agent, the buffer, the taste-masking agent, and any other ingredient introduced in the formulation must have a good solubility in water, have compatibility with other components, and have mild effects on the final viscosity of the formulation. This viscosity of the formulation is important such that the formulation can be delivered as a topical nasal spray using a metered-dose nasal spray device and is filter-sterilizable. The formulation is preferably a clear solution without any precipitate.

In one embodiment, the pharmaceutical formulation comprises epinastine or its salts in an amount of 0.10-0.15% (w/v), a non-ionic tonicity agent such as propylene glycol at 1-2% (w/v), a buffer (such as sodium phosphates) at 10-25 mM, a viscosity-enhancing agent in a range of 0.05-0.5% (w/v), an optional chelating agent in a range of 0.02-0.5% (w/v), and an optional preservative in a range of 0.005-0.2% (w/v). Such an aqueous composition has a tonicity of 250-350 mOsm/kG and is formulated at pH 5-8.

The pharmaceutical formulations of the present invention are preferred to be chemically stable at room temperature for at least 12 months, preferably 24 months, and more preferably 36 months. Chemical stability, as used herein, means that epinastine maintains at least 80%, preferably 85%, 90%, or 95% of its initial chemical assay value.

The pharmaceutical formulations of the present invention can be prepared by aseptic technique. The purity levels of all materials used in the preparation exceed 90%. The solutions of the invention are prepared by thoroughly mixing the epinastine or salts thereof, buffer(s), tonicity agent(s), viscosity-enhancing agent(s), optionally, chelating agent(s), complexing agent(s), solubilizing agent(s), preservative(s) and antioxidant agent(s). Examples of complexing agents are cyclodextrins, gamma-cyclodextrin, and crosspovidone. Examples of solubilizing agents are polysorbates, cremophor, and glycerin. Examples of antioxidants are tocopherol, butylated hydroxytoulene, butylated hydroxyanisole. Complexing agents, solubilizing agents, antioxidants can be added to the formulation; however, they are not essential for the formulation of the present invention.

The pharmaceutical formulation can be sterilized by filtering the formulation through a sterilizing grade filter, preferably of a 0.1 micron nominal pore size. The pharmaceutical formulation can also be sterilized by terminally sterilization using one or more sterilization techniques including but not limited to a thermal process, or a radiation sterilization process, or using pulsed light to produce a sterile formulation.

The pharmaceutical formulation of the present invention is administered locally to the nose in the form of nasal preparations. The pharmaceutical formulation can be administered to the nasal cavity of a patient topically by any suitable means, but is preferably administered in the form of drops or spray; with spray being more preferred. For topical nasal administration, one or two sprays per nostrile of the formulation are delivered to the surface of the nose one to three times, preferably two times per day, according to the routine discretion of a skilled clinician.

The pharmaceutical formulation is preferably packaged in opaque plastic containers equipped with a nasal spray pump for topical nasal delivery. While a variety of metered-dose nasal spray pumps are available for delivery of an aqueous formulation, a metered-dose nasal spray pump that can deliver a small volume spray is preferred in order to minimize the bitter taste of epinastine. This bitter taste of epinastine is due to post-nasal drip of a solution drainage following nasal administration. The use of a viscous formulation of the present invention coupled with a small volume delivery minimizes the bitter taste perception due to epinastine. When multiple small volumes are administered to provide an overall total volume equal to a single larger volume, the bitterness is reduced or eliminated while the therapeutic efficacy is maintained. For example, when one 140 μL spray is delivered in two 70 μL sprays, the bitter taste is reduced or totally eliminated without affecting the treatment efficacy. The preferred range of dose volume of a nasal spray pump for delivering the present formulation is 50-100 milligrams (about 50-100 μL aqueous solution) per actuation, more preferably 50-90 milligrams (about 50-90 μL aqueous solution) per actuation, and most preferably 60-80 milligrams (about 60-80 μL aqueous solution) per actuation.

The pharmaceutical formulations of the present invention can be used to prevent or treat diseases or disorders related to allergic and inflammatory diseases of the nose. For example, the pharmaceutical formulation is useful for treating seasonal and perennial allergic rhinitis, vasomotor rhinitis, sinusitis, asthma, COPD, or emphysema.

The present invention further provides a method for treating allergic rhinitis in a subject, without the adverse effect of bitter taste. The method comprises the steps of: (a) identifying a subject suffering from allergic rhinitis; and (b) administering to the nose of the subject one to two sprays at ≦115 μL (50-115 μL) per nostril per spray once or twice daily of an aqueous epinastine formulation comprising (a) 0.1-0.15% (w/v) of epinastine or an acid addition salt thereof, (b) 0.05-0.5% (w/v) of hydroxypropylmethylcellulose to maintain the viscosity between 1.5-10 centipoise, (c)1-2% (w/v) of propylene glycol, and (d) a buffer to maintain the pH between 5-8, said aqueous epinastine formulation does not contain a sweetening agent and has a tonicity between 200-400 mOsm/kG, whereby the subject perceives a minimal or no bitter taste of said epinastine and the symptoms of allergic rhinitis are reduced. "A minimal bitter taste," as used herein, refers to an acceptable taste perceived by the subject. In this method, the preferred concentration of hydroxypropylmethylcellulose is 0.1-0.3% (w/v). The preferred concentration of propylene glycol is 1-2, or 1-1.8% (w/v).

In a preferred method, the epinastine is administered to the subject using a metered-dose nasal spray pump. The target volume of the nasal spray pump, for example, is 70 μL (±15%) or 100 μL (±15%). The aqueous epinastine formulation is preferably administered at 60-85 μL per nostril per spray, or 85-115 μL per nostril per spray. The aqueous epinastine formulation can be administered one to three times a day, preferably one to two times a day, and more preferably twice a day.

The invention is illustrated further by the following examples that are not to be construed as limiting the invention in scope to the specific procedures described in them.

EXAMPLES

Example 1

Preparing Aqueous Epinastine Formulation

TABLE 1

Epinastine nasal spray formulation (0.1% epinastine)

| Formulation Name | E-unmasked | E-masked |
|---|---|---|
| Component (% w/v) | | |
| Epinastine hydrochloride | 0.1 | 0.1 |
| Hypromellose | 0.1 | 0.1 |
| Propylene Glycol | 1.5 | 1.5 |
| Sodium phosphate, monobasic, anhydrous | 0.084 | 0.084 |
| Sodium phosphate, dibasic, anhydrous | 0.256 | 0.256 |
| Disodium edetate | 0.05 | 0.05 |
| Benzalkonium chloride | 0.01 | 0.01 |
| SWEETAM ™ | 0 | 0.05 |
| Purified Water | QS | QS |
| Adjust pH to | 7.0 ± 0.5 | 7.0 ± 0.5 |

This formulation was prepared by admixing all the agents, with the exception of epinastine hydrochloride, to produce a colorless homogenous viscous solution. Then epinastine hydrochloride was added to this dispersion and vigorously mixed in a vortex mixer or a homogenizer. The preparation was a viscous, clear, colorless preparation, and was easy to be filtered using a standard filtration apparatus. The preparation was isotonic, and within the physiological pH range.

Example 2

Comparison of Taste Preference of 5 Minute Post-Dose of Epinastine Formulations with and without a Sweetening Agent Subjects Subjects were 18-70 years of age with a history of seasonal allergic rhinitis (SAR) or perennial allergic rhinitis (PAR) and must have had an instantaneous symptom score total of <4 on the Total Nasal Symptom Score (TNSS) questionnaire (see Example 3 of Application). This served to recruit subjects with allergic rhinitis who had mild to no symptoms.

Test Protocols

This was a double-blind, randomized, cross-over, taste preference study. Subjects were randomized into one of two cohorts. Cohorts 1 and 2 received epinastine hydrochloride (epinastine) in concentrations of 0.1% and 0.2%, respectively. In each cohort, subjects received a single dose of epinastine without a taste masking agent (a sweetening agent), epinastine with a taste masking agent and a non-epinastine formulation in a random order. SWEETAM™, which is a commercially available sweetening agent containing monoammonium glycyrrihinate salts pre-blended with suitable adjuvants such as sucrose and dextrose, was used as a taste masking agent in this study. Each dose administration was delivered as two sprays (target volume of approximately 70 μL/spray, which translates to a typical spray weight of 78-82 mg) in each nostril (4 sprays total per dosing) and each dosing period was separated by at least 90 minutes (up to 120 minutes). The two epinastine formulations applied to Cohort 1 are shown in Table 1 (see Example 1). The two E-unmasked and E-unmasked epinastine formulations applied to Cohort 2 were identical to those shown in Table 1 except they contained 0.2% epinastine hydrochloride.

Evaluation Criteria

After each dose administration, subjects completed the NSEQ, examining the sensory attributes of each nasal spray 5, 30, and 90 minutes post dose. The NSEQ consisted of 14 individual questions scored on a scale from 0 (least satisfaction) to 100 (greatest satisfaction) and was reported by subjects at 0-5 minutes, 30 minutes, and 90 minutes after each study drug administration. The individual questions asked were as follows.

Question 1: How uncomfortable is it to use this nasal spray? (0=Extremely uncomfortable; 100=Not uncomfortable at all)

Question 2: How much medicine ran down your throat? (0=An extreme amount; 100=None at all)

Question 3: How much medicine ran out of your nostrils? (0=An extreme amount; 100=None at all)

Question 4: Rate the urge to sneeze. (0=Extremely strong urge; 100=No urge at all)

Question 5: Rate the smell of the nasal spray. (0=Extremely strong smell; 100=No smell at all)

Question 6: Rate your satisfaction of the nasal spray smell. (0=Not satisfied at all; 100=Extremely satisfied)

Question 7: Rate the taste of the nasal spray. (0=Extremely strong taste; 100=No taste at all)

Question 8: Rate your satisfaction of the nasal spray taste. (0=Not satisfied at all; 100=Extremely satisfied)

Question 9: Rate the bitterness of the nasal spray. (0=Extremely bitter; 100=Not at all bitter)

Question 10: Rate the aftertaste of the nasal spray. (0=Extremely strong aftertaste; 100=No aftertaste at all)

Question 11: Rate your satisfaction of the nasal spray aftertaste. (0=Not satisfied at all; 100=Extremely satisfied)

Question 12: Rate the dryness of your nose. (0=Extremely dry; 100=Not at all dry)

Question 13: Rate the dryness of your throat. (0=Extremely dry; 100=Not at all dry)

Question 14: Rate your overall satisfaction of this product based on your assessment of questions 1-13. (0=Not satisfied at all; 100=Extremely satisfied)

The results are summarized in Table 2.

TABLE 2

Analysis Results of Individual Sensory Attribute Scores - 5 Minutes Post-Dose

| | Cohort 1 (N = 65) LSMean (SE) | |
|---|---|---|
| Attribute | E-unmasked | E-masked |
| 1. Uncomfortable | 87.7 (2.65) | 86.9 (2.65) |
| 2. Run down throat | 86.5 (2.79) | 86.6 (2.79) |
| 3. Run out nostrils | 78.1 (3.27) | 77.4 (3.27) |
| 4. Sneeze | 87.8 (3.25) | 87.9 (3.25) |
| 5. Smell | 93.5 (2.56) | 88.4 (2.56) |
| 6. Satisfaction on smell | 93.1 (2.94) | 85.0 (2.94) |
| 7. Taste | 86.9 (3.46) | 79.8 (3.46) |
| 8. Satisfaction on taste | 86.9 (3.51) | 76.7 (3.51) |
| 9. Bitterness | 86.6 (3.39) | 80.3 (3.39) |
| 10. Aftertaste | 86.7 (3.32) | 81.5 (3.32) |
| 11. Satisfaction on aftertaste | 85.9 (3.74) | 77.4 (3.74) |
| 12. Dryness of nose | 87.8 (2.54) | 81.8 (2.54) |
| 13. Dryness of throat | 88.9 (2.59) | 85.1 (2.59) |
| 14. Overall satisfaction | 86.2 (2.43) | 85.3 (2.43) |
| Average score | 87.3 (2.07) | 83.1 (2.07) |

Note: The results were analyzed by the mixed ANOVA model including treatment (epinastine unmasked, epinastine masked, and the non-epinastine groups), treatment sequence, and site as fixed effects, and subject within sequence and site as a random effect. SE is the estimated standard error.

The scores reported by patients from Cohort 1 on 12 out of 14 individual sensory attributes (with exception of Attributes 2 and 4) showed a numerical trend that E-unmasked had better sensory attribute ratings than E-masked at 5 minute post dose, which is the most important time point for evaluating after taste. Furthermore, the average score and the individual score of satisfaction on smell of E-unmasked was statistically significantly higher ($p<0.05$) than that of E-masked in Cohort 1 (0.1% epinastine formulation) at 5 minute post dose. The pair wise comparison between epinastine unmasked and epinastine masked groups was performed using two-sample t tests on the LSMeans estimated from the mixed ANOVA model. However, there was no significant difference in taste preference between E-unmasked vs. E-masked in Cohort 2 (0.2% epinastine formulation) at 5 minute post dose. Further, there was no significant difference in taste preference between E-unmasked vs. E-masked in 30 or 90 minute post dose in both Cohorts 1 and 2.

Example 3

Clinical Trial Results

A Phase 2 clinical trial involving a 14-day, randomized, double-blind comparison of two doses of epinastine nasal spray (0.05% or 0.1%) or placebo in subjects who had a documented history of seasonal allergic rhinitis to mountain cedar pollen was conducted. Each group started with approximately 190 subjects. Each subject was administered twice daily, two sprays per nostril (total 4 sprays per administration), of a target volume of 70 μL/spray of placebo, 0.05%, or 0.1% epinastine formulation (see Table 3), using a metered-dose spray pump for 14 days. The epinastine formulations did not contain any taste-masking agent.

TABLE 3

Epinastine nasal spray formulation for the clinical studies

| Formulation Name | Epinastine nasal spray, Placebo | Epinastine nasal spray, 0.5 mg/mL (0.05%) | Epinastine nasal spray, 1 mg/mL (0.1%) |
|---|---|---|---|
| Component (% w/v) | | | |
| Epinastine hydrochloride | 0.0 | 0.05 | 0.1 |
| Hypromellose | 0.1 | 0.1 | 0.1 |
| Propylene Glycol | 1.6 | 1.5 | 1.5 |
| Sodium phosphate, monobasic, anhydrous | 0.084 | 0.084 | 0.084 |

TABLE 3-continued

Epinastine nasal spray formulation for the clinical studies

| Formulation Name | Epinastine nasal spray, Placebo | Epinastine nasal spray, 0.5 mg/mL (0.05%) | Epinastine nasal spray, 1 mg/mL (0.1%) |
|---|---|---|---|
| Sodium phosphate, dibasic, anhydrous | 0.256 | 0.256 | 0.256 |
| Disodium edetate | 0.05 | 0.05 | 0.05 |
| Benzalkonium chloride | 0.01 | 0.01 | 0.01 |
| Purified Water | QS | QS | QS |
| Adjust pH to | 7.0 ± 0.5 | 7.0 ± 0.5 | 7.0 ± 0.5 |

Taste

Of the subjects randomized in the trial, 95% completed the trial and no serious adverse events were reported. While the most common adverse event observed was bitter taste, it was only reported by 4% of subjects in the 0.05% group and by 5% of subjects in the 0.1% group. The results demonstrated a low incidence of taste complaints with the two doses evaluated and showed acceptable tolerability of the formulation.

Efficacy of Treatment

The primary endpoint of the trial was the daily reflective change from baseline for total nasal symptom score (TNSS), averaged over the 14-day treatment period. The endpoint of TNSS conforms to the U.S. Food and Drug Administration's (FDA) draft guidance document for seasonal allergic rhinitis and includes runny nose, nasal congestion, itchy nose and sneezing. The TNSS is the sum of four nasal symptom scores (runny nose, nasal congestion, itchy nose, and sneezing), each evaluated by the subject on a 0-3 scale. The TNSS can range from 0 to 12 total points. Results of the trial demonstrated statistically significant improvement ($p<0.05$) in reflective TNSS for the 0.1% dose group, compared to placebo. Changes in TNSS for the 0.05% dose group were not statistically significant.

The non-nasal symptoms were combined to generate the non-nasal symptom score (NNSS). The NNSS is the sum of three non-nasal symptom scores (itchy throat/palate, itchy eyes and watery eyes), each evaluated by the subject on a 0-3 scale. The NNSS can range from 0 to 9 total points. Total Symptom Score (TSS) is the sum of TNSS and NNSS and can range from 0-21 total points.

There were multiple secondary endpoints in this trial. The secondary endpoints include change from baseline for both NNSS and TSS, change from baseline for individual symptom scores, change from baseline in the night-time symptom score, and change from baseline in quality of life as assessed by the self-administered standardized Rhinoconjunctivitis Quality of Life Questionnaire. Among these, statistically significant improvements ($p<0.05$) compared to placebo were demonstrated in the 0.1% epinastine dose group for the secondary endpoints of non-nasal symptom score (NNSS), TSS, and individual symptoms of runny nose, itchy nose, sneezing, itchy eyes, and watery eyes.

The plasma samples from 43 subjects included in this clinical trial were collected for pharmacokinetic analysis following the first dose (Day 1) and the last dose (Day 14). Plasma epinastine levels following intranasal administration were determined. The plasma epinastine concentrations were generally proportional to the nasal dose administered. The plasma concentrations of epinastine were <1 ng/mL, which was well below those required to produce systemic pharmacological effects by an oral administration. The nasal delivery of the current formulation using a small volume metered-dose nasal spray pump produced low, dose-proportional systemic levels of epinastine.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A method for treating allergic rhinitis without causing an adverse effect of bitter taste in a subject, comprising the steps of:
    identifying a subject suffering from allergic rhinitis;
    administering to the nose of the subject one to two sprays at 50-115 μL per nostril per spray once or twice daily of an aqueous epinastine formulation;
    wherein said aqueous epinastine formulation consists essentially of (a) about 0.1% (w/v) of epinastine or an acid addition salt thereof, (b) 0.05-0.5% (w/v) of hydroxypropylmethylcellulose to maintain the viscosity between 1.5-10 centipoise, (c)1-2% (w/v) of propylene glycol, and (d) a buffer to maintain the pH between 5-8, said aqueous epinastine formulation has a tonicity between 200-400 mOsm/kG, said formulation does not contain a sweetening agent;
    whereby the subject perceives a minimal or no bitter taste and the symptoms of allergic rhinitis are reduced.

2. The method according to claim 1, wherein said subject perceives a higher average sensory attribute score when administered with said epinastine formulation than administered with the same epinastine formulation including a sweetening agent.

3. The method according to claim 1, wherein said hydroxypropylmethylcellulose has a concentration of 0.1-0.3% (w/v).

4. The method according to claim 1, wherein said buffer has a concentration of 1-100 mM to maintain a pH between 5-8.

5. The method according to claim 1, wherein the aqueous epinastine formulation is administered at 60-85 μL per nostril per spray.

6. The method according to claim 5, wherein the aqueous epinastine formulation is administered at about 70 μL per nostril per spray.

7. The method according to claim 1, wherein the aqueous epinastine formulation is administered at 85-115 μL per nostril per spray.

8. The method according to claim 7, wherein the aqueous epinastine formulation is administered at about 100 μL per nostril per spray.

9. The method according to claim 1, wherein said aqueous epinastine formulation further consisting essentially of a chelating agent.

10. The method according to claim 1, wherein said subject is administered with the aqueous epinastine formulation twice daily.

11. The method according to claim 1, wherein said subject is administered with two sprays of the epinastine formulation per nostril at each administration.

12. The method according to claim 1, wherein the allergic rhinitis is seasonal allergic rhinitis, perennial allergic rhinitis, or vasomotor rhinitis.

* * * * *